(12) United States Patent
Kawakami et al.

(10) Patent No.: US 7,666,354 B2
(45) Date of Patent: Feb. 23, 2010

(54) COMPOSITION FOR STERILIZATION COMPRISING ω-ALKOXYPEROXYCARBOXYLIC ACID

(75) Inventors: Masayuki Kawakami, Kanagawa (JP); Kazuya Takeuchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/720,400

(22) PCT Filed: Dec. 22, 2005

(86) PCT No.: PCT/JP2005/024160
§ 371 (c)(1),
(2), (4) Date: May 29, 2007

(87) PCT Pub. No.: WO2006/068306
PCT Pub. Date: Jun. 29, 2006

(65) Prior Publication Data
US 2008/0009549 A1    Jan. 10, 2008

(30) Foreign Application Priority Data

| | | | |
|---|---|---|---|
| Dec. 22, 2004 | (JP) | ............................. | 2004-371332 |
| Jun. 20, 2005 | (JP) | ............................. | 2005-178687 |
| Sep. 2, 2005 | (JP) | ............................. | 2005-254395 |

(51) Int. Cl.
*A61L 2/18* (2006.01)
*C07C 409/24* (2006.01)

(52) U.S. Cl. ........................................... 422/28; 562/2

(58) Field of Classification Search ...................... None
See application file for complete search history.

(56) References Cited

U.S. PATENT DOCUMENTS

| | | | | |
|---|---|---|---|---|
| 2,448,252 | A | * | 8/1948 | Cornthwaite et al. ........... 562/4 |
| 5,545,349 | A | * | 8/1996 | Kurii et al. ............. 252/186.38 |
| 6,635,286 | B2 | * | 10/2003 | Hei et al. ..................... 424/616 |
| 2002/0142935 | A1 | * | 10/2002 | Oubrahim et al. ........... 510/439 |

FOREIGN PATENT DOCUMENTS

| | | |
|---|---|---|
| EP | 0 195 597 A1 | 9/1986 |
| EP | 0 822 183 A2 | 2/1998 |
| JP | 04-279556 | 10/1992 |
| JP | 10-501805 A | 2/1998 |
| JP | 2000-505136 A | 4/2000 |
| JP | 2003-502310 A | 1/2003 |
| JP | 2004-315519 A | 11/2004 |

OTHER PUBLICATIONS

Rüsch gen. Klass et al, Journal of Molecular Catalysis B: Enzymatic, Biocatalytic Peroxy Acid Formation for Disinfection, 2002, 19-20 pp. 499-505.*
Ruesch gen. Klaas, et al "Lipase-catalyzed preparation of Peroxy Acids and their Use for Epoxidation," Journal of Molecular Catalysis A: Chemical, 1997, vol. 117, pp. 311-319.
Schneider, et al "Polar and Steric Effects in Oxidations with Aliphatic Peracids," Chemische Berichte, 1981, vol. 114(4), pp. 1562-1566, Abstract.
Turro, et al "Autoxidation of Ketenes. Diradicaloid and Zwitterionic Mechanisms of Reactions of Triplet Molecular Oxygen and Ketenes," Journal of the American Chemical Society, 1978, vol. 100 (17), pp. 5580-5582.
Database WPI Week 199310, Thomson Scientific, London, GB; AN 1993-080661, XP002511255.
Journal of the American Chemical Society, 1978, 100(17), P5580-5582.
Journal of the Chemical Society, 1958, P102-105.
Japanese Office Action dated, Nov. 10, 2009.

* cited by examiner

*Primary Examiner*—Paul A Zucker
(74) *Attorney, Agent, or Firm*—Sughrue Mion, PLLC

(57) ABSTRACT

A peroxycarboxylic acid represented by the general formula (I):

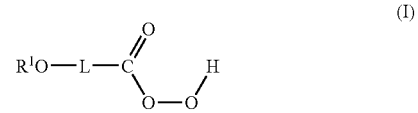

(wherein $R^1$ represents a substituted or unsubstituted C1-C10 alkyl group, or a substituted or unsubstituted C6-C10 aryl group, L represents a substituted or unsubstituted C2-C12 divalent linking group, or $R^1$ and L may combine to form a ring) and a composition comprising said peroxycarboxylic acid are provided. Said peroxycarboxylic acid can sterilize a medical apparatus such as endoscope in a short period of time and has no unpleasant smell.

18 Claims, 1 Drawing Sheet

COMPOSITION FOR STERILIZATION COMPRISING ω-ALKOXYPEROXYCARBOXYLIC ACID

TECHNICAL FIELD

The present invention relates to a composition for sterilization. More specifically, the present invention relates to an aqueous composition for sterilization which is suitable for sterilizing a medical apparatus such as endoscope.

BACKGROUND ART

A medical apparatus such as endoscope, which is not disposable, is directly contacted with patients and therefore needs a safer sterilization for use in subsequent examinations and the like. However, especially in small scale hospitals, a single apparatus is often repeatedly used in a short period of time. Under these circumstances, a composition which have action of killing wide variety of microorganisms and ability of sterilizing a medical apparatuses in a short period of time is desired as a composition for sterilization of a medical apparatus. Further, from a viewpoint of safety, an amount of chemical compounds in the composition is required to be as small as possible.

As a composition for cleaning and sterilizing a medical apparatus such as endoscope, a composition containing an aldehyde such as glutaraldehyde as an active ingredient is conventionally known as a commercial product. However, glutaraldehyde is recently reported to have a weak sterilizing effect to spores and may be a cause of allergies.

A composition for sterilization is also known which contains a peracetic acid as an active ingredient. However, because peracetic acid has irritating smell derived from a peracid as well as strong smell of acetic acid, a practical use of a peracetic acid as a disinfectant will be a burden on an operator, and further an equipment such as ventilation is essential. An aliphatic peroxycarboxylic acid such as peroxypropionic acid is reported to have effective sterilizing action (J. Hyg. Epid. Microbiol. Immun., 9, pp. 220-226 (1965)). However, the aliphatic peroxycarboxylic acids as mentioned above also have a problem of unpleasant smell. The unpleasant smell of the aliphatic peroxycarboxylic acid will be weaker as where the number of carbon atoms increases. When the acid is liner, those having 11 or more carbon atoms have almost no smell. However, they have another problem of insolubility in water and cannot be used for preparation of an aqueous composition which is suitable for sterilization of a medical apparatus.

As a means for solving the problem of the unpleasant smell of the aliphatic peroxycarboxylic acid, use of a peroxycarboxylic acid which is a divalent carboxylic acid is disclosed in Japanese Patent Unexamined Publication (Kokai) No. (Hei) 8-67667. However, a result of an experiment by the inventors of the present invention reveals that an antibacterial effect of the peroxycarboxylic acid is weaker than that of peracetic acid. Japanese Patent Unexamined Publication (Kohyo) No. (Hei) 10-501805 discloses that a peroxycarboxylic acid having an ester group has almost the same degree of antibacterial effect as that of peracetic acid. However, the acid has a problem that, when a peroxycarboxylic acid is synthesized, the ester moiety is susceptible to hydrolysis because a strong acid such as sulfuric acid is used as a reaction catalyst in an aqueous solution.

Peroxymethoxyacetic acid, which is disclosed in J. Molecular Catalysis B: Enzymatic, 19-20, pp. 499-505 (2002), is reported to have weaker antibacterial effect than that of peracetic acid. Nippon Kagaku Zassi (Journal of chemistry in Japan) 87, pp. 476-505, (1966) reports that for a peroxycarboxylic acid such as peroxy chloroacetic acid, substitution with an electron withdrawing group at 2-position will deteriorates stability of the acid. Therefore, peroxymethoxyacetic acid, which is substituted with electron withdrawing methoxy group at 2-position, is expected to have less stability than peracetic acid. As described above, the attempts for reducing the unpleasant smell of peracetic acid have not successfully become practical applications from viewpoints of poor antibacterial effect and lack of formulation suitability.

From an aspect of compounds, an aliphatic peroxycarboxylic acid which has an alkoxy group at 3-position has not been reported so far, and its sterilization activity is not known. Japanese Patent Unexamined Publication (Kohyo) No. 2000-505136 discloses peroxycarboxylic acids represented by the formula Y—Ra—COOOH (wherein Y represents $HO(CH_2CH_2O)_n$ (wherein n represents an integer of 1 to 40, Ra represents a C1-C30 alkylene group). However, Y is limited to an ethylene oxide group in the acid, and the publication only discloses compounds wherein Y is hydroxyalkyloxy group. Further, the publication does not disclose data relating to sterilization effects of the acids. The aforementioned J. Molecular Catalysis B: Enzymatic, 19-20, pp. 499-505 (2002) discloses peroxymethoxyacetic acid, however, it fails to disclose an aliphatic peroxycarboxylic acid having an alkoxy group at 3-position.

DISCLOSURE OF THE INVENTION

An object of the present invention is to provide a peroxycarboxylic acid having no unpleasant smell and an aqueous composition for sterilization comprising said peroxycarboxylic acid. The composition of the present invention is preferably used for sterilization of a medical apparatus such as endoscope.

In order to achieve the foregoing object, the inventors of the present invention conducted intensive researches. As a result, they provided a novel ω-alkoxyperoxycarboxylic acid and found that said ω-alkoxyperoxycarboxylic acid had no unpleasant smell and excellent sterilization effect. The present invention was achieved on the basis of this finding.

The present invention thus provides a peroxycarboxylic acid represented by the general formula (I):

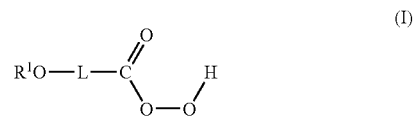

wherein $R^1$ represents a substituted or unsubstituted C1-C10 alkyl group (provided that a substituent having OH group is excluded from the substituent), or a substituted or unsubstituted C6-C10 aryl group, L represents a substituted or unsubstituted C2-C12 divalent linking group, or $R^1$ and L may combine to form a ring.

As preferred embodiments of the present invention, provided are the aforementioned peroxycarboxylic acid, wherein L represents CH $R^{11}$-$L^{12}$ (wherein $R^{11}$ represents hydrogen atom or a substituted or unsubstituted C1-C4 alkyl group, $L^{12}$ represents a substituted or unsubstituted C1-C11 divalent linking group); and the aforementioned peroxycarboxylic acid, wherein $R^1$ is a unsubstituted C1-C4 alkyl group.

The present invention also provides a peroxycarboxylic acid represented by the general formula (II) or (III):

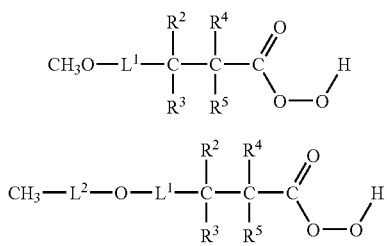

wherein $R^2$, $R^3$, $R^4$, and $R^5$ each independently represents hydrogen, a C1-C4 alkyl group, a C1-C4 alkoxy group, or a C1-C4 alkoxy-substituted C1-C4 alkyl group, $L^2$ represents a substituted or unsubstituted C1-C9 alkylene group, or a substituted or unsubstituted C6-C9 arylene group, and $L^1$ represents a substituted or unsubstituted C1-C10 divalent linking group.

As preferred embodiments of the present invention, provided are the aforementioned peroxycarboxylic acid, wherein $L^1$ is a $CHR^{12}$-$L^{13}$ (wherein $R^{12}$ represents hydrogen atom or a substituted or unsubstituted C1-C4 alkyl group, $L^{13}$ represents a substituted or unsubstituted C1-C9 divalent linking group); the peroxycarboxylic acid, wherein $R^2$, $R^3$, $R^4$, and $R^5$ each independently is hydrogen, a C1-C4 alkyl group, or a C1-C4 alkoxy-substituted C1-C4 alkyl group, $L^2$ is an unsubstituted C1-C2 alkylene group; and the peroxycarboxylic acid, wherein each of $R^2$, $R^3$, $R^4$, and $R^5$ is hydrogen.

The present invention also provides a peroxycarboxylic acid represented by the general formula (IV) or (V):

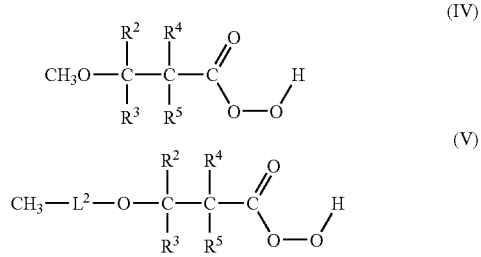

wherein $R^2$, $R^3$, $R^4$, and $R^5$ each independently represents hydrogen, a C1-C4 alkyl group, a C1-C4 alkoxy group, or a C1-C4 alkoxy-substituted C1-C4 alkyl group, $L^2$ represents a substituted or unsubstituted C1-C9 alkylene group, or a substituted or unsubstituted C6-C9 arylene group.

As preferred embodiments of the present invention, provided are the aforementioned peroxycarboxylic acid, wherein $R^2$, $R^3$, $R^4$, and $R^5$ each independently is hydrogen, a C1-C4 alkyl group, or a C1-C4 alkoxy-substituted C1-C4 alkyl group, $L^2$ is an unsubstituted C1-C3 alkylene group; the aforementioned peroxycarboxylic acid, wherein $R^2$ is hydrogen; the aforementioned peroxycarboxylic acid, wherein each of $R^2$, $R^3$, and $R^4$ is hydrogen; the aforementioned peroxycarboxylic acid, wherein $R^5$ is methyl group; the aforementioned peroxycarboxylic acid, wherein $L^2$ is methylene group; the aforementioned peroxycarboxylic acid, wherein each of $R^2$, $R^3$, $R^4$, and $R^5$ is hydrogen; the aforementioned peroxycarboxylic acid, wherein $L^2$ is methylene group; the aforementioned peroxycarboxylic acid, wherein $R^4$ is a C1-C4 alkoxy-substituted methyl group; and the aforementioned peroxycarboxylic acid, wherein $R^5$ is methyl group.

From another aspect, the present invention provides an aqueous composition comprising the aforementioned peroxycarboxylic acid. As preferred embodiments of the present invention, provided are the aforementioned aqueous composition, which further comprises hydrogen peroxide; an aqueous composition which comprises the aforementioned peroxycarboxylic acid, a carboxylic acid corresponding to said peroxycarboxylic acid, and hydrogen peroxide; the aforementioned aqueous composition, wherein a concentration of said peroxycarboxylic acid is in a range of 1 to 2000 mM; the aforementioned aqueous composition, which is characterized in that the concentration of said peroxycarboxylic acid is determined by using an indicator based on chemical or electrochemical principle; the aforementioned aqueous composition, wherein a concentration of said hydrogen peroxide is in a range of 3 to 6000 mM; the aforementioned aqueous composition, wherein a concentration of said peroxycarboxylic acid is 1 to 15 weight %, a concentration of said carboxylic acid corresponding to said peroxycarboxylic acid is 10 to 50 weight %, and a concentration of said hydrogen peroxide is 1 to 15 weight %; the aforementioned aqueous composition, wherein a concentration of said peroxycarboxylic acid is 1 to 15 weight %, a concentration of said carboxylic acid corresponding to said peroxycarboxylic acid is 10 to 50 weight %, a concentration of said hydrogen peroxide is 1 to 15 weight %, and a sum of the concentrations of said peroxycarboxylic acid and said hydrogen peroxide is 25 weight % or less, and a sum of the concentrations of said peroxycarboxylic acid and said carboxylic acid is 50 weight % or less; the aforementioned aqueous composition, which is characterized in that the concentration of said peroxycarboxylic acid is determined by using an indicator based on chemical or electrochemical principle; and the aforementioned aqueous composition, wherein pH is 2 or more and 4.5 or less. As a further preferred embodiment of the present invention, the aforementioned aqueous composition, which comprises one or more additives selected from a group consisting of a corrosion inhibitor, a pH regulator, a metal chelating agent, a stabilizing agent, and a surfactant is provided.

From another aspect, the present invention provides a composition in a dry form for the preparation of the aforementioned aqueous composition. From further aspect of the present invention, provided are a sterilizer which comprises the aforementioned composition; said sterilizer which is for a medical apparatus; and said sterilizer, wherein said medical apparatus is an endoscope.

From further aspect of the present invention, provided are a kit which comprises a composition comprising a carboxylic acid and an aqueous composition comprising hydrogen peroxide for preparation of the aforementioned aqueous composition; a kit which comprises the aforementioned aqueous composition and a composition comprising one or more agents selected from the group consisting of a corrosion inhibitor, a pH regulator, a metal chelating agent, a stabilizing agent, and a surfactant; the aforementioned kit, which is provided as a sterilizer; the aforementioned kit, which is provided as a sterilizer for a medical apparatus; the aforementioned kit, wherein the medical apparatus is an endoscope; and a preparation method of the aforementioned peroxycarboxylic acid, which is characterized to use an acid catalyst.

From still further aspect of the present invention, provided are a sterilization method which comprises a step of contacting a substance to be sterilized with the aforementioned aqueous composition; a sterilization method which comprises a step of contacting a substance to be sterilized with an aqueous composition prepared by adding, to the aforementioned aqueous composition which has been used plural times, a composition comprising said peroxycarboxylic acid at a concentration of 1.5 to 200 times concentration of the aqueous composition before being used; the aforementioned sterilization method, which further comprises a step of washing the substance to be sterilized before the step of contacting a substance to be sterilized with said aqueous composition; the aforementioned sterilization method, which further comprises a step of washing or drying the substance to be sterilized after the step of contacting the substance to be sterilized with said aqueous composition; a method for storing the aforementioned aqueous composition at an ordinary temperature or lower, preferably at 10° C. or lower; a method for storing the aforementioned kit at an ordinary temperature or lower, preferably at 10° C. or lower; a method for discarding the aforementioned aqueous composition after an inactivation treatment of the peroxycarboxylic acid in the aqueous composition; a method for discarding the aforementioned kit after an inactivation treatment of the peroxycarboxylic acid in the kit; and the aforementioned aqueous composition in a form filled in a container made of polyethylene.

BEST MODE FOR CARRYING OUT THE INVENTION

Figure 1:
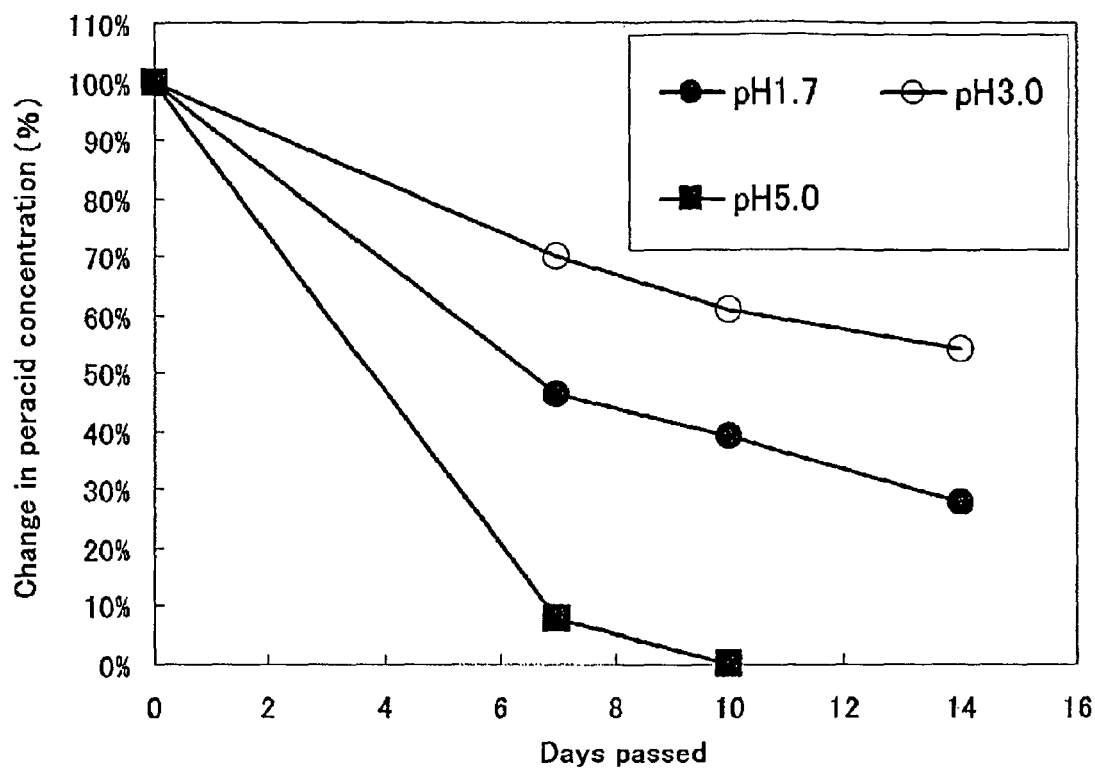
FIG. 1 is a plot showing changes in peroxycarboxylic acid concentrations in aqueous compositions having different pHs.

As the unsubstituted C1-C10 alkyl group represented by $R^1$, examples include methyl group, ethyl group, propyl group, isopropyl group, butyl group, isobutyl group, sec-butyl group, tert-butyl group, pentyl group, isopentyl group, neopenty group, tert-penty group, hexyl group, heptyl group, octyl group, nonyl group, decyl group, 2-ethylhexyl group and the like. The C1-C10 alkyl group represented by $R^1$ may have a substituent provided that a substituent having OH group (hydroxy group, carboxy group, hydroperoxy group, hydroperoxycarbonyl group and the like) is excluded. As substituents of the C1-C10 alkyl group represented by $R^1$, examples include a halogen atom, an alkoxy group, and an alkylsulfonyl group.

As the unsubstituted C6-C10 aryl group represented by $R^1$, an example includes phenyl group. The C6-C10 aryl group represented by $R^1$ may have a substituent. Examples of the substituent include an alkyl group, an alkoxy group, sulfonyl group, hydroxy group, carboxyl group and the like.

As $R^1$, a substituted or unsubstituted C1-C4 alkyl group is preferred, and an unsubstituted C1-C4 alkyl group is more preferred. As the C1-C4 alkyl group represented by $R^1$, examples include methyl group, ethyl group, propyl group, isopropyl group, butyl group, isobutyl group, sec-butyl group, tert-butyl group and the like. As $R^1$, methyl group or ethyl group is most preferred. However, $R^1$ is not limited to these examples.

In the general formula (I), L represents a substituted or unsubstituted divalent linking group having 2 to 12 carbon atoms. As the substituent, examples include an alkyl group, an alkoxy group, hydroxy group, an alkoxy-substituted alkyl group, carboxyl group and the like. The linking group may have an atom other than carbon atom such as an oxygen atom or nitrogen atom in the group.

As L, a preferable example includes $CHR^{11}$-$L^{12}$ ($R^{11}$ represents hydrogen atom or a substituted or unsubstituted C1-C4 alkyl group, and $L^{12}$ represents a substituted or unsubstituted C1-C11 divalent linking group). As $L^{12}$, a substituted or unsubstituted C1-C4 divalerit linking group is preferred, a substituted or unsubstituted methylene group is more preferred, methylene group or methyl-substituted methylene group ($CH(CH_3)$) is further preferred, and methylene group is most preferred.

In the general formula (II), (III), or (V), $L^1$ represents a substituted or unsubstituted C1-C10 divalent linking group. As the substituent, examples include an alkyl group, an alkoxy group, hydroxy group, an alkoxy-substituted alkyl group, carboxyl group and the like. The linking group may have an atom other than carbon atom such as an oxygen atom or nitrogen atom in the group. As $L^1$, a preferable example includes $CHR^{12}$-$L^{13}$ ($R^{12}$ represents hydrogen atom or a substituted or unsubstituted C1-C4 alkyl group, and $L^{13}$ represents a substituted or unsubstituted C1-C9 divalent linking group). As $L^{13}$, a substituted or unsubstituted C1-C4 divalent linking group is preferred, a substituted or unsubstituted methylene group is more preferred, methylene group or methyl-substituted methylene group ($CH(CH_3)$) is further preferred, and methylene group is most preferred.

As the C1-C4 alkyl group represented by $R^2$, $R^3$, $R^4$, or $R^5$, examples include methyl group, ethyl group, propyl group, isopropyl group, butyl group, isobutyl group, sec-butyl group, and tert-butyl group and a preferable example includes methyl group. However, the alkyl group is not limited to these examples. As the C1-C4 alkoxy group represented by $R^2$, $R^3$, $R^4$, or $R^5$, examples include methoxy group ethoxy group, propoxy group, and butoxy group, and preferable examples includes methoxy group and ethoxy group. However, the alkoxy group is not limited to these examples. As the C1-C4alkoxy-substituted C1-C4 alkyl group represented by $R^2$, $R^3$, $R^4$, or $R^5$, examples include methoxymethyl group ethoxymethyl group, propoxymethyl group, butoxymethyl group and ethoxyethyl group, and preferable examples includes methoxymethyl group and ethoxymethyl group. However, the alkoxy-substituted alkyl group is not limited to these examples.

In the general formula (III) or (V), as the divalent linking group represented by $L^2$, a substituted or unsubstituted C1-C9 alkylene group is preferred, a substituted or unsubstituted C1-C3 alkylene group is more preferred, an unsubstituted C1-C3 alkylene group is further more preferred. As the unsubstituted C1-C3 alkylene group represented by $L^2$, examples include methylene group or ethylene group, and a preferable example includes methylene group.

The peroxycarboxylic acid of the present invention may have one or more asymmetric carbons depending on the types of the substituents. Any of the stereoisomers such as optically pure stereoisomers based on one or more asymmetric carbons, any mixtures of said stereoisomers, racemates, diastereoisomers based on two or more asymmetric carbons, any mixtures of said diastereoisomers and the like falls within the scope of the present invention. Further, the peroxycarboxylic acid according to the present invention may exist as hydrates or solvates, and these substances also fall within the scope of the present invention.

Specific examples of the peroxycarboxylic acid of the present invention are shown below. However, the scope of the present invention is not limited to the following compounds.

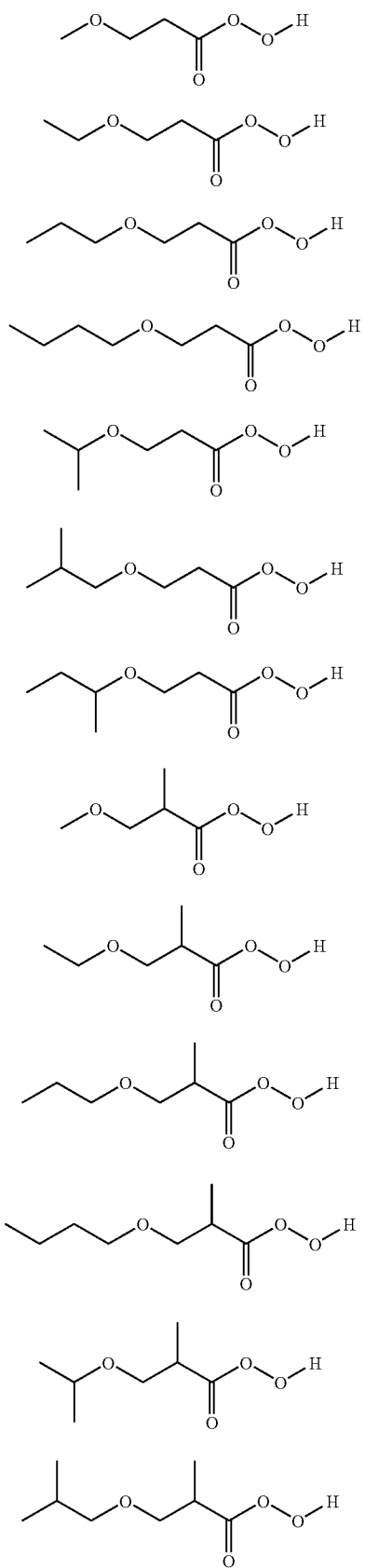
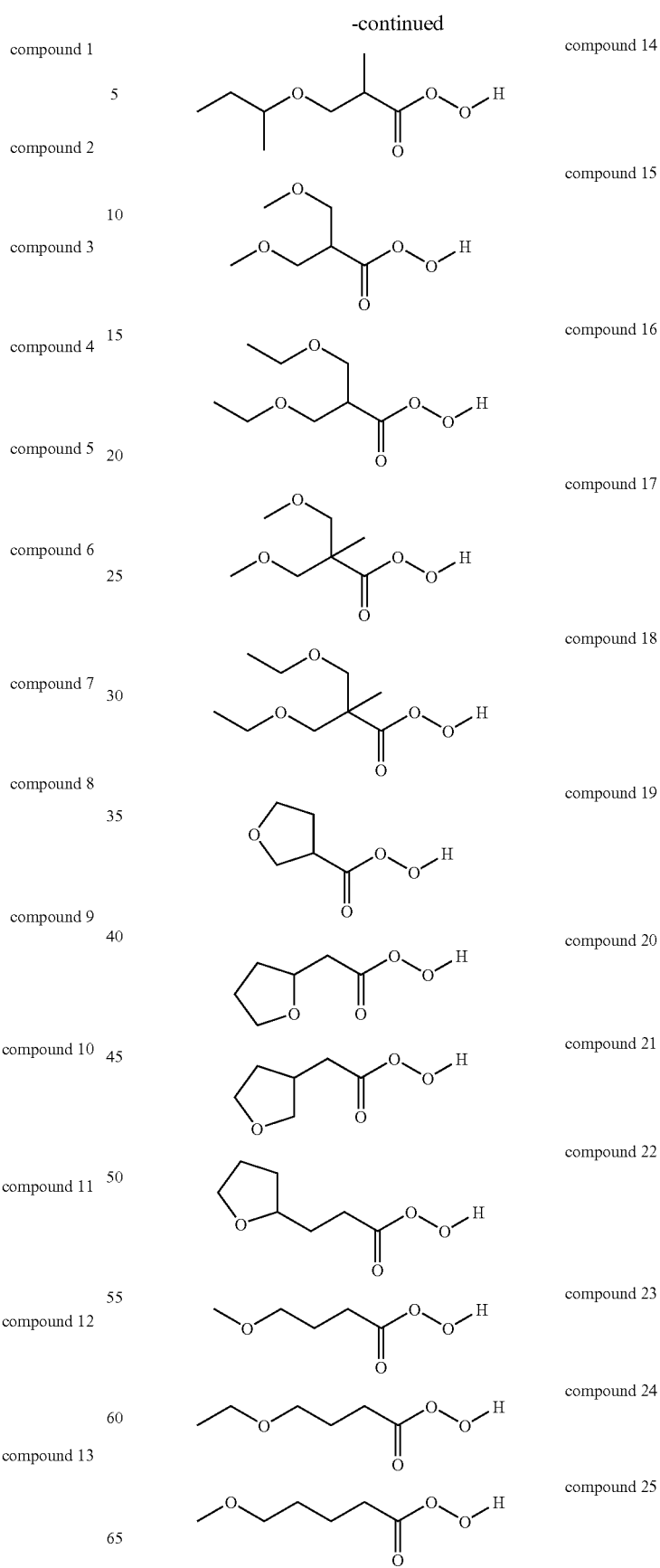

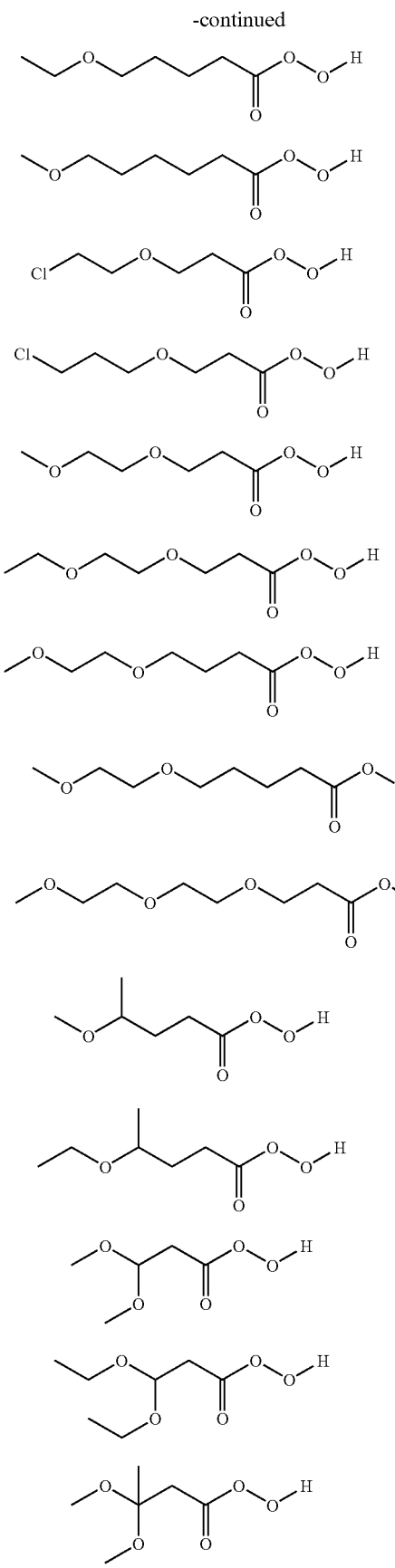

The peroxycarboxylic acid of the present invention can be prepared according to known methods for preparing peroxycarboxylic acid such as that described in Organic peroxides, vol. 1, pp 313-474 (Daniel Swern, John Wiley & Sons, Inc., New York, 1970), and the like. Specifically, a peroxycarboxylic acid can be prepared, for example, by a reaction of a carboxylic acid with hydrogen peroxide. In the reaction of a carboxylic acid with hydrogen peroxide, use of a strong acid is effective as a catalyst of the reaction. As the strong acid, a strongly acidic ion-exchange resin having sulfonic acid group and a solid acid catalyst such as Nafion, as well as sulfuric acid, phosphoric acid or the like can be used As a carboxylic acid used in the above preparation of a peroxycarboxylic acid, a carboxylic acid suitably prepared by a known method, as well as a commercially available carboxylic acid, can be used. For example, 3-alkoxypropionic acid can be prepared by a reaction of β-propiolactone and an alcohol as described in J. Am. Chem. Soc., 70, 1004 (1948) or by a hydrolysis of a 3-alkoxypropionic acid ester obtained from a reaction of an acrylic acid ester and an alkoxide as described in J. Am. Chem. Soc., 69, 2967 (1947), ibid., 77, 754 (1955).

A carboxylic acid which is alkoxy-substituted at a position further than 3-position from a carbonyl group can be prepared by a reaction of a β-δ lactone and an alcohol as described in J. Org. Chem., 59, 2253 (1994).

The aqueous composition of the present invention comprises one or more of the aforementioned peroxycarboxylic acids. In the present specification, "an aqueous composition" means a composition in a state of solution comprising water. A concentration of the peroxycarboxylic acid in the aqueous composition of the present invention may be 0.1 mM or more and 2000 mM or less, preferably 1 mM or more and 200 mM or less, and more preferably 40 mM or more and 120 mM or less.

The aqueous composition of the present invention may comprise, other than the aforementioned peroxycarboxylic acid, a carboxylic acid corresponding to said peroxycarboxylic acids and/or hydrogen peroxide. In the present specification, "a carboxylic acid corresponding to a peroxycarboxylic acid" means a compound which has carboxyl group instead of peroxycarboxylic group of said peroxycarboxylic acid. A concentration of a carboxylic acid corresponding to a peroxycarboxylic acid may be 0.1 mM or more and 2000 mM or less, preferably 1 mM or more and 200 mM or less, more preferably 40 mM or more and 200 mM or less. A concentration of hydrogen peroxide may be 3 mM or more and 6000 mM or less, preferably 10 mM or more and 1000 mM or less, more preferably 30 mM or more and 600 mM or less. The aqueous composition of the present invention preferably comprises peroxycarboxylic acid at a concentration of 1 mM or more and 200 mM or less, and hydrogen peroxide at a concentration of 10 mM or more and 1000 mM or less.

The aqueous composition of the present invention may be prepared so as to have the aforementioned concentrations of the peroxycarboxylic acid and the like when used as, for example, a sterilizer. It has been long known that a peroxycarboxylic acid is generated from hydrogen peroxide and a carboxylic acid. The reaction proceeds as an equilibrium reaction of a carboxylic acid, hydrogen peroxide, a peroxycarboxylic acid, and water, and when a higher concentration of hydrogen peroxide or a carboxylic acid, a higher concentration of a peroxycarboxylic acid will generate. For example, when 90 weight % of hydrogen peroxide is mixed with acetic acid at mole 1.5 times that of hydrogen peroxide, a mixture at equilibrium of peracetic acid of 45 weight %, acetic acid of 35 weight %, hydrogen peroxide of 6 weight %, water of 14 weight % is obtained (kirk-Othmer Encyclopedia of chem. Tech. Inst, Suppl. P662 (1957)).

The aqueous composition of the present invention may comprise one or more additives other than the aforementioned ingredients. Examples of the additives includes corrosion inhibitors, solubilizing agents, pH regulators, metal chelating agents, stabilizing agents, surfactants, antiredeposition agents and the like.

As a corrosion inhibitor, an agent suitable for a material of the medical apparatus to be sterilized may be chosen. Examples include agents comprising a combination of 1,2,3-benzotriazole and one or more compounds selected from a group consisting of a lower alkyl benzotriazole, hydroxybenzotriazole, a lower alkyl hydroxybenzotriazole, carboxybenzotriazole, a lower alkyl carboxybenzotriazole, benzimidazole, a lower alkyl benzimidazole, hydroxybenzimidazole, a lower alkyl hydroxybenzimidazole, carboxybenzimidazole, a lower alkyl carboxybenzimidazole, mercaptobenzothiazole, a lower alkyl mercaptobenzothiazole, hydroxymercaptobenzothiazole, a lower alkyl hydroxymercaptobenzothiazole, carboxymercaptobenzothiazole, a lower alkyl carboxymercaptobenzothiazole, sodium gluconate, sodium benzoate, butyl benzoate, monoethanolamine, triethanolamine, morpholine, sorbitol, erythritol, sodium phosphate, sodium tripolyphosphate, tetrasodium pyrophosphate, sodium molybdate, sodium nitrite, sodium bisulfite, sodium metabisulfite, a chromate, and a borate. However, the corrosion inhibitor is not limited to these examples. In the present specification, the term "lower alkyl" means a liner or branched, and saturated or unsaturated hydrocarbon group having 1 to 6 carbon atoms.

When the composition of the present invention is used for a treatment of an apparatus such as those containing copper, brass, bronze, or polymetal system, a corrosion inhibitor is preferably used which comprises 1,2,3-benzotriazole and one or more compounds selected from a group consisting of a lower alkyl benzotriazole, hydroxybenzotriazole, a lower alkyl hydroxybenzotriazole, sodium molybdate, sodium nitrite, sodium bisulfite, sodium metabisulfite, a chromate, and a borate. Particularly, a corrosion inhibitor comprising 1,2,3-benzotriazole, sodium molybdate, or sodium nitrite is preferably used. When the composition of the present invention is used for a treatment of an apparatus such as those containing carbon steal and/or stainless steal, for example, a corrosion inhibitor comprising sodium benzoate, sodium nitrite, sodium molybdate or the like is preferably used, and a corrosion inhibitor comprising sodium nitrite and/or sodium molybdate is also preferred. A total amount of a corrosion inhibitor in the aqueous composition of the present invention is generally 0.1 weight % to about 30 weight % of the total mass of the composition, and an amount of 1,2,3-benzotriazole is preferably 0.1 weight % to about 3.0 weight %, and more preferably 0.5 weight % to about 2.0 weight %.

When a corrosion inhibitor has a poor solubility in the aqueous composition of the present invention comprising a peroxycarboxylic acid, the composition of the present invention may further comprise a solubilizing agent such as alkylene glycol. In the specification, the term "alkylene glycol" means, for example, ethyleneglycol, propyleneglycol, dialkyleneglycol (for example, diethyleneglycol), trialkyleneglycol (for example, triethyleneglycol), and the glycols such as the corresponding mono- and di-alkylether of the aforementioned glycols, wherein the alkyl ether is a lower alkyl ether having 1 to 6 carbon atoms (for example, methyl-, ethyl-, or propyl-ether). According to a particularly preferred embodiment, the composition of the present invention comprises propylene glycol as a solubilizing agent, and the propylene glycol is preferred to be contained in the composition of the present invention at a concentration about 3 to 10 times that of the corrosion inhibitor. For example, when 1,2,3-benzotriazole is contained in the aqueous composition of the present invention at about 1 weight %, propyleneglycol is preferred to be contained in the aqueous composition of the present invention at about 3.5 weight % to 6.5 weight %.

As a pH regulator, an agent can be used which is suitable for the composition of the present invention and environmentally acceptable. For example, an organic acid such as citric acid, acetic acid, tartaric acid, malic acid, lactic acid, glycolic acid, succinic acid, glutaric acid, or adipic acid, and a salt thereof, an ionic acid such as phosphoric acid or sulfuric acid, and a salt thereof, and a base such as ammonium hydroxide or hydroxide of an alkaline metal can be used. However, pH regulators which can be used in the present invention are not limited to the above examples. A concentration of the pH regulator in the composition of the present invention is preferred to be 20 weight % or less, and particularly preferred to be 0.1 weight % to 10 weight % based on the total mass of the composition.

The composition of the present invention is preferably comprises a heavy metal ion chelating agent as an optional ingredient. In the present specification, a heavy metal ion chelating agent means an ingredient having an action of chelating a heavy metal ion, and means an ingredient which more selectively bonds to a heavy metal ion such as iron, manganese, and copper, even when the agent also has an ability of chelating calcium and magnesium. Heavy metal ion chelating agents are generally present in the composition of the present invention at a level of 0.005 weight % to 20 weight %, preferably 0.1 weight % to 10 weight %, more preferably 0.25 weight % to 7.5 weight %, most preferably 0.5 weight % to 5 weight % based on the total mass of the composition.

As a heavy metal ion chelating agent suitably added to the composition of the present invention, examples include organic phosphonates such as aminoalkylene poly(alkylene phosphonate), alkaline metal ethane 1-hydroxy diphosphonate and nitrilotrimethylene phosphonate. Among them, aminotri(methylene phosphonate), diethylenetriaminepenta(methylene phosphonic acid), ethylenediaminetri(methylene phosphonate), hexamethylenediaminetetra(methylene phosphonic acid), and hydroxy-ethylene-1,1-diphosphonate are preferred.

As other heavy metal ion chelating agent preferably added to the composition of the present invention, examples include nitrilotriacetic acid, polyamino carboxylic acid such as ethylenediaminetetraacetic acid, ethylenetriaminepentaacetic acid, ethylenediaminedisuccinic acid, ethylenediaminediglutaric acid, 2-hydroxypropylenediaminedisuccinic acid, or a salt thereof. Ethylenediamine-N,N'-disuccinic acid (EDDS), or an alkaline metal, alkaline earth metal, ammonium, or substituted ammonium salt thereof, or a mixture thereof is particularly preferred.

As other heavy metal ion chelating agents preferably added to the composition of the present invention, examples include 2-hydroxyethyldiacetic acid, and iminodiacetic acid derivatives such as glyceryl iminodiacetic acid which are described in European Patent Unexamined Publication Nos. 317,542 and 399,133; iminodiacetic acid-N-2-hydroxypropylsulfonic acid and asparagine acid —N-carboxymethyl-N-2-hydroxypropyl-3-sulfonic acid chelating agent which are described in European Patent Unexamined Publication No. 516,102; and β-alanine-N,N'-diacetic acid, asparagic acid-N,N'-diacetic acid, asparagic acid-N-monoacetic acid, and imino disuccinic acid chelating agent which are described in European Patent Unexamined Publication No. 509,382. In European Patent Unexamined Publication No. 476,257, a suitable chelating agent having an amino group is described. In European Patent Unexamined Publication No. 510,331, a suitable chelating agent derived from collagen, keratin, or casein is described. In European Patent Unexamined Publication No. 528,859, a suitable alkyliminodiacetic acid chelating agent is described. Dipicolinic acid and 2-phosphonobutane-1,2,4-tricarboxylic acid are also preferred. Glycinamide-N,N'-disuccinic acid (GADS), ethylenediamine-N,N'-diglutaric acid (EDDG), and 2-hydroxypropylenediamine-N,N'-disuccinic acid (HPDDS) are also preferred. However, a heavy metal ion chelating agent suitably add to the composition of the present invention is not limited to the above examples.

As a stabilizing agent, any known stabilizing agent may be used, and examples include phosphates, 8-hydroxyquinoline, stannic acid, sulfolene, sulfolane, sulfoxide, sulfone, sulfonic acid and the like. In the composition of the present invention, a preferable stabilizing agent is a phosphate. Preferably, the composition of the present invention contains phosphates at about 0.001 weight % to about 0.5 weight % based on the total mass of the composition. The aforementioned phosphate is selected from a group consisting of sodium orthophosphate, potassium orthophosphate, sodium pyrophosphate, potassium pyrophosphate, sodium polyphosphate, potassium polyphosphate, and a combination thereof.

Further, the composition of the present invention may optionally contain a surfactant up to about 30 weight % based on the total mass of the composition. As the surfactant, a surfactant may be used which is stable to oxidation and decomposition in an acidic aqueous solvent in the presence of a peroxycarboxylic acid and hydrogen peroxide, and a surfactant susceptible to oxdation is preferably avoided. A suitable surfactant can be selected from non-ionic-type, anionic-type, zwitter ion-type, and cationic-type surfactants. As a preferable surfactant to be added to the composition of the present invention, examples include non-ionic-type surfactants, specifically, polyethylene/polypropylene block polymer type surfactant, polyoxyethylenealkylphenylether type surfactant, polyoxyethylene ether type surfactant, polyoxyethylenesorbitan type surfactant, and the like. However, surfactants to be added to the composition of the present invention are not limited to the above examples.

As an antiredeposition agent, an agent may be used which has an action of maintaining substances such as stains, which are desorbed from a medical apparatus, being suspended in a liquid. For example, organic aqueous colloids (such as starch, gelatin, an ethercarboxylic acid salt or an ethersulfonic acid salt of starch, cellulose, a cellulose ether, an ethercarboxylic acid salt or ethersulfonic acid salt of cellulose, or an acidic sulfonic ester salt of cellulose or starch) can be used. A water-soluble polyamide having an acidic group can also be preferably used. Further, starch derivatives other than the aforementioned derivatives such as an aldehyde starch can be used. However, the antiredeposition agents to be added to the composition of the present invention are not limited to these examples. As the antiredeposition agent, one or more types agents selected from the aforementioned compounds exemplified as antiredeposition agents can be used. A concentration of the antiredeposition agent in the aqueous composition of the present invention is preferred to be 5 weight % or less, and particularly preferred to be 2 weight % or less.

The term "sterilization" used in the present specification includes meanings of "washing", "disinfection", and "antibacterial function" and the like. By choosing conditions such as a concentration of peroxycarboxylic acid, a time for contact with a medical apparatus and the like, "complete sterilization" of a medical apparatuses can be achieved by using the aqueous composition of the present invention. Spores as being bacteria having particularly high resistance, for example *Bacillus subtilis*, can be killed in a short period of time by using the composition of the present invention. The term "sterilizer" used in the specification means a sterilizer which achieves sterilizing action to various microorganisms mainly by its chemical action, and encompasses any sterilizer having high-, middle-, and low level effect which are classified by Spaulding. The Spaulding classification is as follows: a sterilizer which can mainly kill proliferative common bacteria is classified into a low level (low grade) sterilizer; a sterilizer which can kill a highly resistant bacterium such as *Bacillus* tuberculosis into a middle level (middle grade) sterilizer; and a sterilizer which can kill the most highly resistant bacterium spore is a high level (high grade) sterilizer. An intended application of the sterilizer comprising the aqueous composition of the present invention is not particularly limited, and the sterilizer can be used for sterilization of a polluted vapor phase, as well as a liquid and a solid. Pollutants and the like in a vapor phase can be treated by spraying a diluted solution of the aqueous composition of the present invention or by babbling a vapor through the bath of the aqueous composition of the present invention.

As liquids which can be sterilized with the aqueous composition of the present invention, examples include microorganism-stained aqueous substances such as recirculating process water or process water consisting of pre-disposal aqueous outflow fluid and outflow fluid. Such process water and outflow fluid are produced in many industries, and may be stained with bacteria, algae, or yeast, or more rarely with virus. Further, treatments of plant and animal substances always produces stained process water. Industries which produce such process water and outflow fluid are not particularly limited and examples include paper and pulp industry, and food treatment industry (for example, sugar purification industry, brewing, wine production, and alcohol distillation industry). Other examples include outflow fluid from straw treatment, wastewater from a sewage-treatment plant (for example, partially treated or simply filtered sewage water as wastewater via duct line to sea), wastewater from a slaughter plant, animal fat refining industry, or livestock breeding. As other liquids which can be sterilized by the aqueous composition of the present invention, examples include irrigation water in gardening industry, aqueous fertilizer and circulating water in tank farming, and water for aquafarming in fishing industry. As other important liquids which can be sterilized by the aqueous composition of the present invention, examples include coolant water discharged from industrial activities or air conditioning equipments in large buildings (for example, hotels, business offices, and hospitals). The aqueous composition of the present invention can be used for sterilization treatment of nonaqueous liquid substance such as cutting oil.

The aqueous composition of the present invention can be used for disinfection of harvested plants or plant products (for example, seeds, corms, tubers, fruits, and vegetables). The aqueous composition of the present invention can be used for treatment of plants which are being growing, particularly for plants as harvests are being growing (for example, cereal grass, leafy vegetables, vegetable crop for salad, root crop, beans, sup fruits, citrus plants, and nuts). Further, as easily understood by an artisan, the aqueous composition of the present invention can be used for, if necessary, a different purpose such as bleaching, and the composition can be used also as a bleaching additive in laundry.

In addition, the aqueous composition of the present invention can be used for disinfection of a solid, for example, a substance having a hard surface, or a soiled substance which is intended to be reused in the field of food treatment, animal bleeding, gardening, catering, homes, and hospitals. As the substance having a hard surface, examples include substances made of metal, wood, ceramics, glass, fabrics, and plastics, including food packages, contact lenses, workbenches, walls, floors, sanitary wares, pools, industrial plants, clothing materials, sheets, covers, apparatuses, containers, industrial tools, machines, plants and piping. As a soiled substance which is intended to be reused in the field of hospitals, examples include various medical apparatuses such as apparatus for wearing lens, endoscopes, surgical instruments such as knife and catheter, obstetrical or urological instruments, anesthesia apparatuses, artificial ventilators, dialysis treatment apparatuses, dental instruments or supportive instruments thereof, syringes, clinical thermometers, and other plastic instruments. The aqueous composition of the present invention is suitable for sterilization of dental instrument and surgical instruments such as endoscope, which need sterilizations in a short period of time. As is easily understood by an artisan, the substance which has a hard surface and is rather small in a size can be soaked in a solution of the aqueous composition of the present invention for a convenient sterilization handling. When the aqueous composition of the present invention is used for a treatment of a larger substance, spray or a similar dispersion procedure thereto can be more easily conducted. Such sterilization procedure can also be used as a method for disinfecting hygroscopic material such as soiled linen or particularly soiled baby diapers (which is often made of terry towel cloth).

The sterilization method using the aqueous composition of the present invention is not particularly limited as described above. For example, a sterilization method is preferred wherein a substance to be sterilized is soaked in the aqueous composition of the present invention to achieve a contact of the substance with the composition. In said soaking, the aqueous composition of the present invention may be stirred, the substance to be sterilized may be shaken, or an automatic washer may be used. Further, as suggested in "Guideline for washing and disinfection of endoscope, the second edition", an automatic washer may be used after washing by hands. The automatic washer is not particularly limited, and a commercial washer can be used. The method may include a step of washing the substance to be sterilized before or after said soaking. The method may further include a step of wiping the substance to be sterilized with sterilized gauze or a step of drying the substance to be sterilized with a dryer. In the present specification, "washing" means a procedure to reduce stains of the substance to be sterilized. The means used for washing is not particularly limited, and water, alkaline detergent, neutral detergent, alcohol detergent, enzyme detergent, ultrasonic washing or the like may be preferably used. A temperature for the sterilization is not particularly limited, and 0° C. or more is preferred, and the aqueous composition of the present invention is more preferred to be used at an ordinary temperature. An ordinary temperature means a temperature in a range of an ordinary life. For example, an ordinary temperature is generally about 15 to 25° C. in facilities such as hospitals. The aqueous composition of the present invention can be used at a temperature higher than the ordinary temperature, if necessary. A period of time for contacting the substance to be sterilized with the aqueous composition of the present invention is not particularly limited provided that the period of time is about 15 seconds or more. The period of time is preferred to be 20 minutes or less, more preferred to be 10 minutes or less and particularly preferred to be 5 minutes or less. The aqueous composition of the present invention may contact once with a substance to be sterilized. Alternatively, sterilization can be repeated twice or more.

The aqueous composition of the present invention can be repeatedly used as a sterilizer. When a concentration of the peroxycarboxylic acid of the present invention as an active ingredient in the composition decreases by being used plural times, the composition can be added with an aqueous composition comprising the peroxycarboxylic acid of the present invention at a high concentration (for example, a concentration 1.5 to 200 times that of the aqueous composition before the aforementioned use) and the concentration of the active ingredient can be increased for successive use as a sterilizer.

The aqueous composition of the present invention per se can be provided as a sterilizer. Further, an aqueous composition comprising a carboxylic acid corresponding to a peroxycarboxylic acid represented by the general formulae (I), (II), (III), (IV), or (V) and an aqueous composition comprising hydrogen peroxide can be provided as a kit to be mixed when used. The mixture may be used after a dilution with water, if necessary. A peroxycarboxylic acid represented by the general formulae (I), (II), (III), (IV), or (V) and the aforementioned additives can be provided in a dry form to be dissolved in an aqueous solvent when used.

Further, the aqueous composition of the present invention can be provided as an kit which comprises an aqueous composition comprising a peroxycarboxylic acid represented by the general formulae (I), (II), (III), (IV), or (V), a carboxylic acid corresponding to said peroxycarboxylic acid, and hydrogen peroxide (which hereinafter referred to as "the first reagent") and an composition comprising one or more selected from a group consisting of corrosion inhibitors, pH regulators, metal chelating agents, stabilizing agents, and surfactants (which hereinafter referred to as "the second reagent"), and these reagents can be mixed when used. The mixture may be used after a dilution with water, if necessary. A reagent other than the first and the second reagents can be mixed, if necessary.

The aqueous composition of the present invention per se can be provided as a sterilizer. However, the aqueous composition can be used in combination with other sterilizer. For example, the aqueous composition of the present invention can be mixed with another sterilizer and used. The mixture may be used after a dilution with water, if necessary. Alternatively, a treatment with another sterilizer can be added before or after the sterilization with the aqueous composition of the present invention. The sterilizer to be combined with the aqueous composition for sterilization of the present invention is not particularly limited, however, peracetic acid, aqueous hydrogen peroxide, glutaraldehyde, orthophthalaldehyde, ethanol for disinfection are preferred, and peracetic acid and aqueous hydrogen peroxide are particularly preferred.

The aforementioned first reagent comprises preferably 1 to 15 weight % of the peroxycarboxylic acid of the present invention, 10 to 50 weight % of a carboxylic acid corresponding to said peroxycarboxylic acid, and 1 to 15 weight % of hydrogen peroxide; more preferably 3 to 13 weight % of the peroxycarboxylic acid of the present invention, 20 to 50 weight % of a carboxylic acid corresponding to said peroxycarboxylic acid, and 3 to 15 weight % of hydrogen peroxide; further preferably 5 to 11 weight % of the peroxycarboxylic acid of the present invention, 20 to 40 weight % of a carboxylic acid corresponding to said peroxycarboxylic acid, and 5 to 15 weight % of hydrogen peroxide.

Further, the aforementioned first reagent comprises preferably 1 to 15 weight % of the peroxycarboxylic acid of the present invention, 10 to 50 weight % of a carboxylic acid corresponding to said peroxycarboxylic acid, and 1 to 15 weight % of hydrogen peroxide, and simultaneously, a sum of said peroxycarboxylic acid and hydrogen peroxide is 25 weight % or less and a sum of said peroxycarboxylic acid and said carboxylic acid is 50 weight % or less; more preferably 3 to 13 weight % of the peroxycarboxylic acid of the present invention, 20 to 50 weight % of a carboxylic acid corresponding to said peroxycarboxylic acid, and 3 to 15 weight % of hydrogen peroxide, and simultaneously, a sum of said peroxycarboxylic acid and hydrogen peroxide is 25 weight % or less and a sum of said peroxycarboxylic acid and said carboxylic acid is 50 weight % or less; further preferably 5 to 11 weight % of the peroxycarboxylic acid of the present invention, 20 to 40 weight % of a carboxylic acid corresponding to said peroxycarboxylic acid, and 5 to 15 weight % of hydrogen peroxide, and simultaneously, a sum of said peroxycarboxylic acid and hydrogen peroxide is 25 weight % or less and a sum of said peroxycarboxylic acid and said carboxylic acid is 45 weight % or less.

When the first and the second reagent as described above are mixed and diluted with water and then used, the change of equilibrium from a peroxycarboxylic acid to a carboxylic acid corresponding to said peroxycarboxylic acid is accelerated with an acidic catalyst under pH 2, and as a result, the concentration of the peroxycarboxylic acid is remarkably decreased, and the period of time for which the composition can be continuously used is shortened. Further, when a pH is higher than 5, a carboxylic acid, whose dissociation constant is generally around 4, dissociates to form a salt of the carboxylic acid, and a concentration of the carboxylic acid is decreased, which as a result raises a problem that the change of equilibrium from a peroxycarboxylic acid to a carboxylic acid is accelerated. Accordingly, as for an aqueous composition prepared by mixing the first and the second reagents and diluting the mixture with a solvent such as water, a pH range is preferred to be 2 to 4.5. For adjusting a pH, the aforementioned regulator, specifically, an agent which is suitable for the composition of the present invention and environmentally acceptable, such as an organic acid such as citric acid, acetic acid, tartaric acid, malic acid, lactic acid, glycolic acid, succinic acid, glutaric acid, or adipic acid, and a salt thereof, an ionic acid such as phosphoric acid or sulfuric acid, and a salt thereof, and a base such as ammonium hydroxide or hydroxide of an alkaline metal, can be used.

As for concentrations of a peroxycarboxylic acid in the aqueous composition of the present invention or the like, measurement method is not particularly limited. However, a method using an indicator based on chemical or electrochemical principle is preferred. As the method based on chemical principle, examples include measurement methods using coloring by oxidation-reduction and coloring by change of pH. As the method based on electrochemical principle, examples include measurement methods using pulse current measurement, resistance measurement of a solution, electric potential difference current measurement, and the like.

Disposal treatment of the peroxycarboxylic acid, the aqueous composition, or the sterilizer of the present invention is not particularly limited. When diluted with a large amount of water, a peroxycarboxylic acid changes to the corresponding carboxylic acid by the change of the chemical equilibrium, which therefore achieves disposal with lower load to environment. The peroxycarboxylic acid, the aqueous composition, or the sterilizer of the present invention can be discarded after an inactivation treatment. The inactivation treatment means a treatment for reducing the amount of peroxycarboxylic acid, and the method for inactivation is not particularly limited. Examples include methods such as treatment with a reducing agent, irradiation with ultraviolet ray, adjustment to a high pH, irradiation with ultrasonic wave and the like.

A container for storing the peroxycarboxylic acid of the present invention is not particularly limited. However, a container which does not react with a peroxycarboxylic acid is preferred. For example, when the aqueous composition comprising the peroxycarboxylic acid of the present invention is provided in the market as a sterilizer or the like, the sterilizer is preferred to be provided in a form filled in a container made of polyethylene.

EXAMPLES

The present invention will be explained more specifically with reference to examples. However, the scope of the present invention is not limited to the following examples.

Example 1

Synthesis of 3-methoxyperoxypropionic acid (Compound 1)

3-Methoxypropionic acid (2.82 mL, 30 mmol) was added with 50% aqueous hydrogen peroxide (2.58 mL, 45 mmol) and left at room temperature for 3 days. Potassium iodide/sodium thiosulfate titration was conducted according to the method of B. Dudley et al. (Analyst, 87, 653-657 (1962)) to determine concentrations of 3-methoxyperoxypropionic acid and hydrogen peroxide after the 3 days.

Result: 3-Methoxyperoxypropionic acid: 157 mM
Concentration of hydrogen peroxide: 7872 mM Example 2

Synthesis of 3-ethoxyperoxypropionic acid (Compound 2)

3-Ethoxypropionic acid (3.38 mL, 30 mmol) was added with 50% aqueous hydrogen peroxide (2.58 mL, 45 mmol) and left at room temperature for 3 days. Concentrations of 3-ethoxyperoxypropionic acid and hydrogen peroxide after the 3 days were determined in a similar manner to that in Example 1.

Result: 3-Ethoxyperoxypropionic acid: 162 mM
Concentration of hydrogen peroxide: 7787 mM

Example 3

Synthesis of Various Peroxycarboxylic Acids Using an Acid Catalyst and Concentrations of Peroxycarboxylic Acids in the Obtained Aqueous Compositions a) Synthesis of Compound 1 (3-methoxyperoxypropionic acid)

3-Methoxypropionic acid (46 mL, 490 mmol) was added with 50% aqueous hydrogen peroxide (42.4 mL, 735 mmol) and concentrated sulfuric acid (0.52 mL, 9.8 mmol) and left at room temperature for 10 days. Concentrations of 3-methoxyperoxypropionic acid and hydrogen peroxide after the 10 days were determined in a similar manner to that in Example 1.

Result: 3-Methoxyperoxypropionic acid: 1800 mM
Concentration of hydrogen peroxide: 6000 mM b) Synthesis of Compound 2 (3-ethoxyperoxypropionic acid)

3-Ethoxypropionic acid (261.9 g, 2220 mmol) was added with 50% aqueous hydrogen peroxide (192 mL, 3330 mmol) and concentrated sulfuric acid (2.36 mL, 44 mmol) and left at room temperature for 10 days. Concentrations of 3-ethoxyperoxypropionic acid and hydrogen peroxide after the 10 days were determined in a similar manner to that in Example 1.

Result: 3-Ethoxyperoxypropionic acid: 1700 mM
Concentration of hydrogen peroxide: 5500 mM c) Synthesis of Compound 3

3-Propoxypropionic acid (25.0 g, 189 mmol) was added with 50% aqueous hydrogen peroxide (16.4 mL, 284 mmol) and concentrated sulfuric acid (0.5 mL, 9.4 mmol) and left at room temperature for 4 days. Potassium iodide/sodium thiosulfate titration as described in Example 1 was conducted to determine the concentration of peroxycarboxylic acid 3 (Compound 3) after the 4 days.

Result: Peroxycarboxylic acid 3: 1.6M d) Synthesis of Compound 5

3-(1-Methylethoxy)propionic acid (4.0 mL, 30 mmol) was added with 50% aqueous hydrogen peroxide (2.6 mL, 45 mmol) and concentrated sulfuric acid (16 μL, 0.3 mmol) and left at room temperature for 7 days. Potassium iodide/sodium thiosulfate titration as described in Example 1 was conducted to determine the concentration of peroxycarboxylic acid 5 (Compound 5) after the 7 days.

Result: Peroxycarboxylic acid 5: 1.4 M e) Synthesis of Compound 19

Tetrahydrofuran-3-carboxylic acid (3.8 mL, 40 mmol) was added with 50% aqueous hydrogen peroxide (3.4 mL, 60 mmol) and left at room temperature for 4 days. Potassium iodide/sodium thiosulfate titration as described in Example 1 was conducted to determine the concentration of peroxycarboxylic acid 19 (Compound 19) after the 4 days.

Result: Peroxycarboxylic acid 19: 0.6 M f) Synthesis of Compound 24

4-Ethoxybutaonic acid (1.32 g, 10 mmol) was added with 50% aqueous hydrogen peroxide (0.86 mL, 15 mmol) and concentrated sulfuric acid (5 μL, 0.1 mmol) and left at room temperature for 3 days. Potassium iodide/sodium thiosulfate titration as described in Example 1 was conducted to determine the concentration of peroxycarboxylic acid 24 (Compound 24) after the 3 days.

Result: Peroxycarboxylic acid 5: 1.4 M g) Synthesis of Compound 25

5-Methoxypentanonic acid (3.0 g, 23 mmol) was added with 50% aqueous hydrogen peroxide (1.96 mL, 34 mmol) and concentrated sulfuric acid (24 μL, 0.5 mmol) and left at room temperature for 6 days. Potassium iodide/sodium thiosulfate titration as described in Example 1 was conducted to determine the concentration of peroxycarboxylic acid 25 (Compound 25) after the 6 days.

Result: Peroxycarboxylic acid 25: 1.8 M h) Synthesis of Compound 26

5-Ethoxypentanonic acid (5.0 g, 34 mmol) was added with 50% aqueous hydrogen peroxide (3.0 mL, 51 mmol) and concentrated sulfuric acid (18 μL, 0.3 mmol) and left at room temperature for 4 days. Potassium iodide/sodium thiosulfate titration as described in Example 1 was conducted to determine the concentration of peroxycarboxylic acid 26 (Compound 26) after the 4 days.

Result: Peroxycarboxylic acid 26: 1.5 M i) Synthesis of Compound 27

6-Methoxyhexanonic acid (5.0 g, 34 mmol) was added with 50% aqueous hydrogen peroxide (3.0 mL, 51 mmol) and concentrated sulfuric acid (18 μL, 0.3 mmol) and left at room temperature for 4 days. Potassium iodide/sodium thiosulfate titration as described in Example 1 was conducted to determine the concentration of peroxycarboxylic acid 27 (Compound 27) after the 4 days.

Result: Peroxycarboxylic acid 27: 1.6 M j) Synthesis of Compound 28

2-(2-Chloroethoxy)propionic acid (4.6 g, 30 mmol) was added with 50% aqueous hydrogen peroxide (2.6 mL, 45 mmol) and concentrated sulfuric acid (16 μL,) and left at room temperature for 2 days. Potassium iodide/sodium thiosulfate titration as described in Example 1 was conducted to determine the concentration of peroxycarboxylic acid 28 (Compound 28) after the 2 days.

Result: Peroxycarboxylic acid 28: 126 mM k) Synthesis of Compound 35

4-Methoxy-4-methylbutanoic acid (5.0 g, 38 mmol) was added with 50% aqueous hydrogen peroxide (3.3 mL, 57 mmol) and concentrated sulfuric acid (20 μL, 0.4 mmol) and left at room temperature for 4 days. Potassium iodide/sodium thiosulfate titration as described in Example 1 was conducted to determine the concentration of peroxycarboxylic acid 35 (Compound 35) after the 4 days.

Result: Peroxycarboxylic acid 35: 1.7 M l) Synthesis of Compound 36

4-Ethoxy-4-methylbutanoic acid (5.0 g, 34 mmol) was added with 50% aqueous hydrogen peroxide (3.0 mL, 51 mmol) and concentrated sulfuric acid (18 μL, 0.3 mmol) and left at room temperature for 4 days. Potassium iodide/sodium thiosulfate titration as described in Example 1 was conducted to determine the concentration of peroxycarboxylic acid 36 (Compound 36) after the 4 days.

Result: Peroxycarboxylic acid 36: 1.3 M

Example 4

Method for Evaluation of Antimicrobial Activity

Antimicrobial activity of the composition of the present invention against spores was evaluated.

Spores of *Bacillus subtilis* IFO3134 was prepared based on the preparation method of a spores stock solution described in Notification from Ministry of Health, Labour and Welfare, "Ei-nyu(Milk Hygiene)" No. 10, Jan. 29, 1996 (Heisei 8).

Specifically, *Bacillus subtilis* IFO3134 was cultured on Nutient Agar (Difco) at 37° C. for one week and spore production at a rate about 90% was observed. The bacteria were suspended in sterilized water (3 ml), and the suspension was heated at 65° C. for 30 minutes under shaking at 160 rpm to kill trophozoites. Resulting suspension was centrifuged at 3000 rpm, and the supernatant was discarded. Sterilized water (3 ml) was added to the residue to obtain a stock solution of spores. A solution of $1.1 \times 10^9$ cfu/mL was prepared using the stock solution and subjected to the following evaluations of antimicrobial activity.

Evaluation of antimicrobial activity was conducted according to the method of Sakagami et al. (J. Antibact. Antifung. Agents., Vol. 26, 605-601, 1998). Specifically, an aqueous solution (225 μl) of each sample which was filtered with 0.2 μm paper filter was added with spores suspension (25 μl) prepared by the above described method. The mixture (concentration of bacteria: $1.1 \times 10^8$ cfu/mL) was reacted for a given period of time. From the reaction solution, 2 μL sample was corrected and added to 2 ml of SCDLP culture medium (Nissui Pharmaceutical Co., Ltd.). The medium was cultured at 37° C. under shaking at 160 rpm for 48 hours, and the presence of bacterial growth was examined. At the same time, the reaction solution (25 μL) was added to a mixture solution (225 μL) of 0.1N sodium thiosulfate and 1% catalase to inactivate a peroxycarboxylic acid and hydrogen peroxide. Resulting solution (100 μL) was inoculated to SCDLP culture agar medium (Nissui Pharmaceutical Co., Ltd., 25 mL/petri dish). The medium was cultured at 37° C. for 48 hours, and examined visually for colony formation.

Each solution prepared in Example 1, 2, 3-c, 3-f, and 3-j was diluted with distilled water for injection (Hikari pharmaceutical company) so as to obtain a solution of peroxycarboxylic acid at a concentration of 40 mM, which was used as composition 1, 2, 3, 24, and 28. The compositions were evaluated for their antimicrobial activity using the above described method. The results are shown in Table 1. Aqueous hydrogen peroxide which contains hydrogen peroxide at a higher concentration than the hydrogen peroxide concentration of the above diluted solutions was separately evaluated in a similar manner, and results are also shown in Table 1.

TABLE 1

|  | Compound | peracid | Concentration | Culturing method | 15 sec | 1 min | 5 min |
|---|---|---|---|---|---|---|---|
| Composition 1 | Compound 1 | Example 1 | 40 mM | Liquid culture | + | + | − |
|  |  |  |  | Agar culture | + | + | − |
| Composition 2 | Compound 2 | Example 2 | 40 mM | Liquid culture | + | + | − |
|  |  |  |  | Agar culture | + | + | − |
| Composition 3 | Compound 3 | Example 3-c | 40 mM | Liquid culture | + | + | − |
|  |  |  |  | Agar culture | + | + |  |
| Composition 24 | Compound 24 | Example 3-f | 40 mM | Liquid culture | + | + | − |
|  |  |  |  | Agar culture | + | + | − |
| Composition 28 | Compound 28 | Example 3-j | 40 mM | Liquid culture | + | + | − |
|  |  |  |  | Agar culture | + | + | − |
| Hydrogen peroxide |  |  | 2000 mM | Liquid culture | + | + | + |
|  |  |  |  | Agar culture | + | + | + |

In Table 1, symbol + indicate that bacterial proliferation in liquid culture or colony formation in agar culture was observed, and symbol − indicate that bacterial proliferation in liquid culture or colony formation in agar culture was not observed

Comparative Example 1

Antimicrobial activity of Acecide (Saraya Co., Ltd.), which is a composition of 40 mM peracetic acid, was evaluated in a similar manner to that in Example 4. Results are shown in Table 2.

TABLE 2

|  | Concentration | Culturing method | 15 sec | 1 min | 5 min |
|---|---|---|---|---|---|
| peracetic acid | 40 mM | Liquid culture | + | + | − |
|  |  | Agar culture | + | + | − |

Comparative Example 2

The following comparative compound was evaluated in a similar manner to that in Example 4. As a result, it was found that the antimicrobial activity was lower than that of Composition 1, Composition 2 or the like.

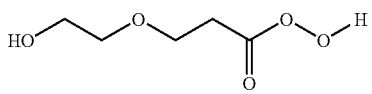

The above results indicate that the compounds of the present invention, alkoxyperoxycarboxylic acids, have antimicrobial activity as high as that of peracetic acid. The above hydroxy-terminated comparative compound, which is in the scope of the claimed invention described in the Japanese Patent Unexamined Publication No. 2000-505136 has lower antimicrobial activity than that of the novel peroxyalkoxycarboxylic acid of the present invention. Further, practical use of peracetic acid as a disinfectant is a burden to an operator and needs an equipment such as ventilation because of its irritating smell derived from peracid and strong smell of acetic acid. Whislt, ω-alkoxyperoxycarboxylic acid has little smell, and an operator can conduct disinfection of a medical apparatus without any burden.

Example 5

Stability Evaluation 1

Method of Stability Evaluation

A carboxylic acid (30 mmol) and 50% aqueous hydrogen peroxide (45 mmol) were mixed, and concentration of generated peracid was quantified by potassium iodide/sodium thiosulfate titration as described in Example 1 at a constant time interval. As the carboxylic acid, 3-methoxypropionic acid and 3-ethoxypropionic acid were used. As a control for comparison, methoxyacetic acid was used. Results of the measurement are shown in Table 3.

cation was conducted by potassium iodide/sodium thiosulfate titration as described in Example 1.

Compound 3 (peroxy-3-propoxypropionic acid: 0.46 M
Hydrogen peroxide: 3.6M

The aqueous composition was diluted with water to adjust the peroxycarboxylic acid concentration at 80 mM. Three solutions of pH 1.7, 3.0, and 5.0 were prepared, and peroxycarboxylic acid concentration was quantified by potassium iodide/sodium thiosulfate titration as described in Example 1 at a constant time intervals. The pH was adjusted by addition of dipotassium hydrogen phosphate. Assuming that peroxycarboxylic acid concentration of 80 mM is 100%, changes in peroxycarboxylic acid concentration are shown in FIG. 1.

FIG. 1 shows that when pH is lower than 2, or 5 or higher, a decrease in peroxycarboxylic acid concentration was faster, which raises a risk in storage stability, whereas a solution at pH 3.0 gave significantly high storage stability.

Example 7

Evaluation Whether to Meet the Standard for the Fifth Class of Hazardous Material A aqueous composition of the peroxycarboxylic acid which was obtained in the above described Synthesis of compound 3 (1.6 M, 100 ml) was mixed with water (50 ml) for dilution, and the mixture was left at 25° C. for 14 days. The solution was further kept at 4° C. for 10 days. Quantification was conducted by potassium iodide/sodium thiosulfate titration as described in Example 1.

Compound 3 (peroxy-3-propoxypropionic acid: 0.49 M
Hydrogen peroxide: 3.9M

On the basis of the above result of titration, the composition of the above solution was analyzed and the following results were obtained.

TABLE 3

| | | | Days after mixing | | | | | | |
|---|---|---|---|---|---|---|---|---|---|
| Carboxylic Acid | peroxycarboxylic acid | Compound No. | 3 | 5 | 6 | 10 | 14 | 22 | 24 |
| Methoxyacetic acid | peroxy-methoxyacetic acid | | 530 | — | 540 | 380 | 340 | — | 210 |
| 3-methoxypropionic acid | peroxy-3-methoxypropionic acid | Compound 1 | 160 | 250 | — | — | — | 650 | — |
| 3-ethoxypropionic acid | peroxy-3-ethoxypropionic acid | Compound 2 | 160 | — | 310 | — | — | 700 | — |

Numbers in Table 3 indicates peracid concentration (mM) in compositions.

Table 3 shows that, as for the peroxy-methoxyacetic acid having alkoxy group at 2-position, a peracid concentration significantly decreased with passage of time, indicating that peroxy-methoxyacetic acid is unstable. As for peroxy-3-methoxypropionic acid and peroxy-3-ethoxypropionic acid, which are compounds of the present invention, any decrease in peracid amount was not observed.

Example 6

Stability Evaluation 2 pH Dependency

A aqueous composition of the peroxycarboxylic acid which was obtained in the above described Synthesis of compound 3 (1.6 M, 100 ml) was diluted by addition of water (50 ml), and the mixture was left at 25° C. for 7 days. Quantifi- Compound 3 (peroxy-3-propoxypropionic acid: 7% w/w;
Hydrogen peroxide: 13% w/w;
3-propoxypropionic acid: 32% w/w; and
Water: 48% w/w.

The above aqueous composition was subjected to judgment whether or not the composition meets the criteria of the fifth class of hazardous material in the Fire Defense Law. The results were "no hazardous" in the thermal analysis, and "rank 3" in the pressure container test, which revealed that the above aqueous composition did not classified in the fifth class of hazardous material in the Fire Defense Law.

INDUSTRIAL APPLICABILITY

The present invention provides a ω-alkoxyperoxycarboxylic acid as a novel compound. The present invention also provides a composition comprising said compound which can sterilize a medical apparatus such as an endoscope in a short period of time and has no unpleasant smell. The composition of the present invention achieves a complete sterilization in a short period of time, particularly for spores such as that of *Bacillus subtilis*.

The invention claimed is:

1. A method of sterilizing an endoscope which comprises a step of contacting a substance to be sterilized with an aqueous composition comprising a peroxycarboxylic acid represented by the general formula (I):

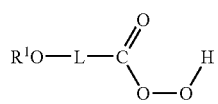

wherein $R^1$ represents a C1-C10 alkyl group which may be substituted with a halogen atom, an alkoxy group, or an alkylsulfonyl group, L represents CH $R^{11}$-$L^{12}$ (wherein $R^{11}$ represents a hydrogen atom or an unsubstituted C1-C4 alkyl group, and $L^{12}$ represents a C1-C11 divalent linking group which may be substituted with an alkyl group, an alkoxy group, a hydroxy group, an alkoxy-substituted alkyl group, or a carboxyl group), or $R^1$ and L may combine to form a ring,
wherein the peroxycarboxylic acid is selected from the group consisting of compounds 1, 2, 3, 24, and 28:

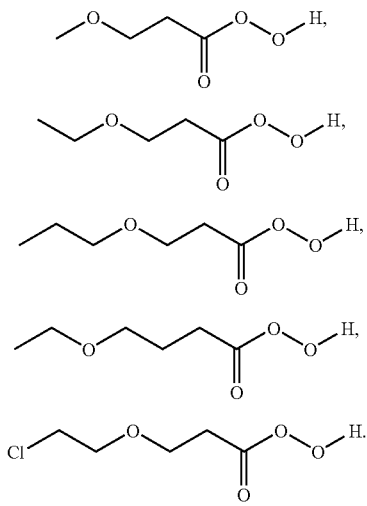

2. The method according to claim 1, wherein the aqueous composition further comprises hydrogen peroxide.

3. The method according to claim 1, wherein the aqueous composition further comprises a carboxylic acid corresponding to said peroxycarboxylic acid, and hydrogen peroxide.

4. The method according to claim 1, wherein the concentration of said peroxycarboxylic acid in the aqueous composition is in a range of 1 to 2000 mM.

5. The method according to claim 4, which is characterized in that the concentration of said peroxycarboxylic acid is determined by using an indicator based on chemical or electrochemical principles.

6. The method according to claim 2, wherein the concentration of said hydrogen peroxide in the aqueous composition is in a range of 3 to 6000 mM.

7. The method according to claim 3, wherein the concentration of said peroxycarboxylic acid in the aqueous composition is in a range of 1 to 15 weight %, the concentration of said carboxylic acid corresponding to said peroxycarboxylic acid is in a range of 10 to 50 weight %, and the concentration of said hydrogen peroxide is in a range of 1 to 15 weight %.

8. The method according to claim 3, wherein the concentration of said peroxycarboxylic acid in the aqueous composition is in a range of 1 to 15 weight %, the concentration of said carboxylic acid corresponding to said peroxycarboxylic acid is in a range of 10 to 50 weight %, the concentration of said hydrogen peroxide is in a range of 1 to 15 weight %, and the sum of the concentrations of said peroxycarboxylic acid and said hydrogen peroxide is 25 weight % or less, and the sum of the concentrations of said peroxycarboxylic acid and said carboxylic acid is 50 weight % or less.

9. The method according to claim 7, which is characterized in that the concentration of said peroxycarboxylic acid is determined by using an indicator based on chemical or electrochemical principle.

10. The method according to claim 1, wherein the pH of the aqueous composition is from 2 or more to 4.5 or less.

11. The method according to claim 1, wherein the aqueous composition comprises a corrosion inhibitor.

12. The method according to claim 1, wherein the aqueous composition comprises a pH regulator.

13. The method according to claim 1, wherein the aqueous composition comprises a metal chelating agent.

14. The method according to claim 1, wherein the aqueous composition comprises a stabilizing agent.

15. The method according to claim 1, wherein the aqueous composition comprises a surfactant.

16. A method of sterilizing an endoscope which comprises a step of contacting a substance to be sterilized with an aqueous composition prepared by adding, to an aqueous composition comprising a peroxycarboxylic acid selected from the group consisting of compound 1, 2, 3, 24, and 28 which has been used plural times, a composition comprising said peroxycarboxylic acid at a concentration of 1.5 to 200 times the concentration of the aqueous composition before being used:

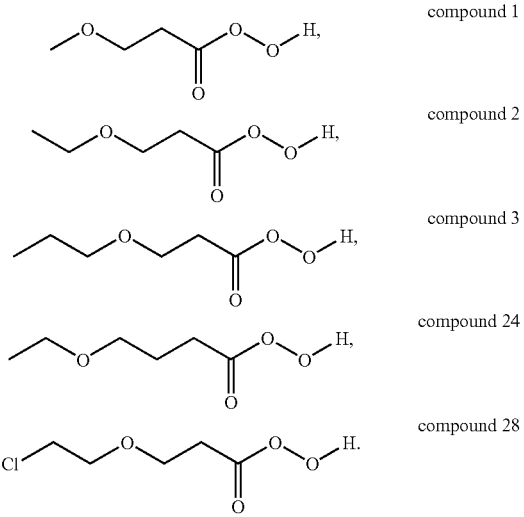

17. The method according to claim 1, which further comprises a step of washing the substance to be sterilized before the step of contacting a substance to be sterilized with said aqueous composition.

18. The method according to claim 1, which further comprises a step of washing or drying the substance to be sterilized after the step of contacting the substance to be sterilized with said aqueous composition.

* * * * *